(12) United States Patent
Hognon et al.

(10) Patent No.: US 10,351,497 B2
(45) Date of Patent: Jul. 16, 2019

(54) USE OF A LEWIS DONOR SOLVENT TO PURIFY A FEEDSTOCK THAT CONTAINS ETHANOL, ACETALDEHYDE, AND IMPURITIES

(71) Applicants: IFP Energies Nouvelles, Rueil-Malmaison (FR); Compagnie Generale des Etablissements Michelin, Clermont-Ferrand (FR)

(72) Inventors: Celine Hognon, Mions (FR); Sophie Drozdz, Brindas (FR); Marc Jacquin, Lyons (FR)

(73) Assignees: IFP Energies Nouvelles, Rueil-Malmaison (FR); Compagnie Generale des Etablissements Michelin, Clermont-Ferrand (FR)

( * ) Notice: Subject to any disclaimer, the term of this patent is extended or adjusted under 35 U.S.C. 154(b) by 0 days.

(21) Appl. No.: 16/300,122

(22) PCT Filed: May 9, 2017

(86) PCT No.: PCT/EP2017/061094
§ 371 (c)(1),
(2) Date: Nov. 9, 2018

(87) PCT Pub. No.: WO2017/194559
PCT Pub. Date: Nov. 16, 2017

(65) Prior Publication Data
US 2019/0144366 A1 May 16, 2019

(30) Foreign Application Priority Data

May 12, 2016 (FR) .................................... 16 54234

(51) Int. Cl.
*B01D 3/14* (2006.01)
*B01D 11/04* (2006.01)
(Continued)

(52) U.S. Cl.
CPC .............. *C07C 29/86* (2013.01); *B01D 3/143* (2013.01); *B01D 11/0488* (2013.01); *B01D 11/0492* (2013.01); *C07C 45/80* (2013.01)

(58) Field of Classification Search
CPC .............. B01D 11/043; B01D 11/0488; B01D 11/0492; C07C 1/20; C07C 29/86; C07C 31/08; C07C 11/167
See application file for complete search history.

(56) References Cited

U.S. PATENT DOCUMENTS 2,403,743 A 7/1946 Hitchcock et al.
9,950,969 B2 * 4/2018 Dastillung ............ C07C 1/2072
(Continued)

FOREIGN PATENT DOCUMENTS

FR 3014098 A1 6/2015
FR 3026100 A1 3/2016
FR 3026101 A1 3/2016

OTHER PUBLICATIONS

International Search Report dated Aug. 23, 2017 issued in corresponding PCT/EP2017/061094 application (3 pages).
(Continued)

*Primary Examiner* — Jafar F Parsa
(74) *Attorney, Agent, or Firm* — Millen, White, Zelano and Branigan, P.C.

(57) ABSTRACT

The invention pertains to the use of a solvent that comprises a Lewis donor compound that is selected from the group made up of unsaturated fatty acids that have between 12 and 18 carbon atoms, phosphate esters that have between 12 and 30 carbon atoms, and mixtures thereof to separate the impurities from a feedstock that contains ethanol, acetaldehyde, and impurities.

9 Claims, 1 Drawing Sheet

(51) Int. Cl.
*C07C 29/86* (2006.01)
*C07C 45/80* (2006.01)

(56) References Cited

U.S. PATENT DOCUMENTS

2017/0267604 A1  9/2017  Dastillung et al.
2017/0291859 A1  10/2017  Dastillung et al.

OTHER PUBLICATIONS

English Abstract of WO 2015/079041 A1 which corresponds to FR 3014098 A1 published Jun. 5, 2015.

* cited by examiner

USE OF A LEWIS DONOR SOLVENT TO PURIFY A FEEDSTOCK THAT CONTAINS ETHANOL, ACETALDEHYDE, AND IMPURITIES

TECHNICAL FIELD OF THE INVENTION

This invention pertains to a new solvent for liquid-liquid extraction for the purpose of eliminating the impurities from an aqueous mixture of ethanol and acetaldehyde, as well as the method that employs this solvent.

PRIOR ART

The methods for producing butadiene from ethanol were developed in particular by American teams during the Second World War based on the works of Ostromilenski.

In this method, the conversion per pass is less than 50%, meaning that there is considerable recycling of ethanol and acetaldehyde. Moreover, with this method, a wide variety of impurities of different kinds (saturated hydrocarbons, unsaturated hydrocarbons, aromatic hydrocarbons, oxygen products [alcohols, ketones, aldehydes, phenols, acids, esters, ethers]) that have very different molar masses (between 50 and 10,000 g/mol) are produced.

It is thus necessary to establish a sequence of unit operations for the purpose of eliminating as much of the impurities as possible while losing as little ethanol and acetaldehyde as possible. From an economic standpoint, it is paramount to reduce the cost of butadiene production, making it necessary to:

lose as little ethanol and acetaldehyde as possible;
not recycle impurities into the reactors that would lead to a drop in butadiene selectivity or that would build up to unacceptable levels, leading to the necessity of a purge and thus to losses of ethanol and acetaldehyde.

At the outlets of catalytic reactors, the effluent produced, which is composed of butadiene, acetaldehyde, water, ethanol, and impurities, undergoes multiple unit operations in order to separate the byproducts that are gaseous at ambient temperature from those that are liquid at ambient temperature.

The gaseous byproducts include hydrogen, carbon monoxide, carbon dioxide, alkanes, and $C_1$-$C_4$ olefins. It is essential to eliminate these byproducts from the butadiene-rich effluent in order to obtain a product that meets specifications.

The byproducts that are liquid at ambient temperature include acetone, diethyl ether, butanal, butanol, butanone, ethyl acetate, crotonaldehyde, and acetic acid. Other byproducts are produced in smaller quantities in the reaction zone. Hereinafter "impurities" will be defined as this set of thousands of hydrocarbon or oxygen compounds.

In the first method schemes developed by the American teams, ethanol, acetaldehyde, water, and the liquid byproducts were separated by a series of three distillation columns (patent U.S. Pat. No. 2,403,742). The effluent, rich in ethanol, acetaldehyde, water, and liquid byproducts, feeds a first distillation column in which an acetaldehyde-rich effluent is separated from the rest of the effluent. A second distillation column makes it possible to separate the liquid byproducts from an effluent that is rich in ethanol and water. The last distillation column makes it possible to separate ethanol from water. The majority of the method patents filed between 1940 and 1960 by the companies Carbide & Carbon or Koppers (U.S. Pat. Nos. 2,403,743; 2,393,381; 2,395,057 and 2,439,587) are aimed at improving upon this portion of the scheme.

Since the liquid impurities form a continuum of volatility from very light to very heavy, it is very difficult to ensure that they are isolated perfectly from ethanol and acetaldehyde. Moreover, since the nature of the impurities ranges from very hydrophobic to very hydrophilic, phase separations arise in both the residue and the distillate, creating operating problems within the distillation columns.

In the patents FR 1,458,859 and FR 1,458,860, the elimination of liquid impurities is done by liquid-liquid extraction. The effluent, which is composed of ethanol, acetaldehyde, water, and impurities, feeds a liquid-liquid extraction column. The latter is fed at the bottom with a washing solvent whose purpose is to provide for counter-current washing of the feedstock. At the outlet of this washing section, the extract is composed in the majority of the washing solvent, the extracted byproducts, and small quantities of ethanol and acetaldehyde. This extract is then washed in water in order to re-extract the ethanol and acetaldehyde and thus to minimize the losses of ethanol and acetaldehyde. The washing solvent that is used for this unit operation consists of a mixture of hydrocarbons that have between 6 and 40 carbon atoms and preferably between 10 and 20 carbon atoms. The washing solvent can be a diesel or desulfurized kerosene fraction or else a hydrocarbon fraction that is produced by a unit such as a Fischer-Tropsch unit.

The regeneration of the washing solvent is carried out by two series-connected distillation columns. The first column, referred to in patent FR 1,458,859 as "Section for distillation of light brown oils," separates the light impurities from a hydrocarbon residue that contains the heavy impurities and the washing solvent. This residue is then distilled in a second column, referred to as "Section for distillation of heavy oils," which produces as a distillate a mixture that is essentially composed of the washing solvent with some traces of impurities and, as a residue, the effluent that is referred to as "heavy brown oils," containing the heavy impurities.

In this configuration, during the liquid-liquid extraction, a precipitate forms and can, over time, foul the extraction columns, the stirring blades, or the fittings. In order to remedy this problem, it is necessary to use a fairly expensive anti-fouling material or to shut down the system on a regular basis to clean it from top to bottom.

OBJECT AND ADVANTAGE OF THE INVENTION

The invention pertains to the use of a specific solvent for the purpose of eliminating the impurities contained in a feedstock that comprises water, ethanol, acetaldehyde, and impurities, as well as a method that uses this solvent.

Surprisingly enough, the applicants have discovered that using a solvent that has the properties of a Lewis donor made it possible to obtain improved performance levels, especially compared to the solvents described in patents FR 1,458,859 and FR 1,458,860. As a matter of fact, using the solvents identified by the applicants makes it possible to prevent the formation of a precipitate, which adversely affects the proper operation of the liquid-liquid extraction column. Moreover, these solvents make it possible to reduce the ratio between the solvent flow rate and the feedstock flow rate, all the while maintaining a good separation quality between the impurities, on the one hand, and the ethanol and acetaldehyde, on the other hand.

DETAILED DESCRIPTION OF THE INVENTION

The invention pertains to a method for purifying a feedstock that contains ethanol, acetaldehyde, and impurities using a solvent, referred to as a Lewis donor solvent, that contains a Lewis donor compound that is selected from the group composed of unsaturated fatty acids that have between 12 and 18 carbon atoms, phosphate esters that have between 12 and 30 carbon atoms, and mixtures thereof, where said method comprises:

A counter-current liquid-liquid extraction step A) that is fed at the top with said feedstock in a mixture with the raffinate obtained from re-extraction step B), where this mixture comprises the feed for said step A), and is fed at the bottom with the effluent rich in the Lewis donor solvent obtained from regeneration step C), with a Lewis donor solvent make-up optionally being mixed with said Lewis donor solvent-rich effluent, and produces at the top an extract and at the bottom a purified feedstock, where said step operates at a temperature of between 10 and 70° C. and a pressure of between 0.1 and 0.5 MPa, with a continuous-phase mass flow rate/dispersed-phase mass flow rate ratio of less than 70;

A counter-current liquid-liquid re-extraction step B) that is fed at the top with an auxiliary solvent and at the bottom with the extract that is obtained from step A), where said step produces at the top an extract and at the bottom a raffinate, where said raffinate feeds said step A), with said step operating at a temperature of between 10 and 70° C. and at a pressure of between 0.1 and 0.5 MPa with a continuous-phase mass flow rate/dispersed-phase mass flow rate ratio of less than 70;

A regeneration step C) in which the extract obtained from step B) is separated by a first distillation into a distillate that is rich in light impurities and a residue that undergoes a second distillation, with the latter producing at the top an effluent that is rich in Lewis donor solvent and a residue that is rich in heavy impurities.

The invention also pertains to the use of a solvent that contains a Lewis donor compound that is selected from the group made up of unsaturated fatty acids that have between 12 and 18 carbon atoms, phosphate esters that have between 12 and 30 carbon atoms, and mixtures thereof in order to separate the impurities from a feedstock that contains ethanol, acetaldehyde, and impurities.

The invention also pertains to the use of a solvent that contains a Lewis donor compound that is selected from the group made up of unsaturated fatty acids that have between 12 and 18 carbon atoms, phosphate esters that have between 12 and 30 carbon atoms, and mixtures thereof in order to separate the impurities from a feedstock that contains ethanol, acetaldehyde, and impurities depending on the steps of said method for purifying a feedstock that contains ethanol, acetaldehyde, and impurities.

Said solvent containing a Lewis donor compound that is used according to the invention or is employed in the method according to the invention makes it possible to eliminate the impurities contained in a feedstock that comprises ethanol, acetaldehyde, and impurities. The impurities vary widely in nature (saturated, unsaturated, and aromatic hydrocarbons, oxygen products, including alcohols, ketones, aldehydes, phenol compounds, acids, esters, and ethers) and have molar masses ranging from 50 to more than 10,000 g/mol. The typical impurities can include acetone, diethyl ether, butanal, butanols, butanones, ethyl acetate, crotonaldehyde, pentenes, pentadienes, hexenes, and hexadienes.

As is well known to one skilled in the art, a "Lewis donor compound" or "Lewis base" is defined as a compound that features an electron doublet that can be displaced toward another compound, which in turn is referred to as a "Lewis acid." For the purposes of the invention, the Lewis donor compound is selected from the group that is made up of unsaturated fatty acids that have between 12 and 18 carbon atoms, phosphate esters that have between 12 and 30 carbon atoms, and mixtures thereof. Said Lewis donor compound is preferably selected from the group that is made up of oleic acid, linoleic acid, tributyl phosphate, and mixtures thereof. More preferably, the Lewis donor compound is oleic acid.

According to a preferred embodiment, the solvent that comprises a Lewis donor compound consists of 100% by weight of a Lewis donor compound that is selected from the group made up of unsaturated fatty acids that have between 12 and 18 carbon atoms, phosphate esters that have between 12 and 30 carbon atoms, and mixtures thereof.

According to another embodiment, also preferred, said Lewis donor solvent also comprises at least one hydrocarbon that contains at least 12 carbon atoms. The proportion (Lewis donor compound)/(hydrocarbon+Lewis donor compound) falls into a range of 1% to less than 100% by weight, preferably 15% to less than 100% by weight, and very preferably 30% to less than 100% by weight.

Said hydrocarbon is selected in such a way as to be insoluble in the feedstock that feeds said step A). Said hydrocarbon is advantageously a $C_{12}$-$C_{50}$ fraction and very advantageously a $C_{14}$-$C_{30}$ fraction. Said hydrocarbon is advantageously a diesel fraction or a fuel oil fraction. Advantageously, the hydrocarbon fraction is selected in such a way that the temperature of the Lewis donor solvent falls within the boiling-point range of the hydrocarbon fraction.

Feedstock to be Purified

The feedstock that is to be purified by the method according to the invention or is to be purified by utilization in accordance with the invention is an aqueous solution containing ethanol, acetaldehyde, and impurities, where the latter are to be eliminated.

Preferably, the ethanol content in said feedstock is between 40 and 70% by weight and preferably between 50 and 60% by weight, the acetaldehyde content is between 1 and 30% by weight and preferably between 5 and 10% by weight, and the content of impurities is between 1 and 20% by weight and preferably between 5 and 20% by weight.

Impurity Extraction Step A)

The purification method according to the invention comprises a counter-current liquid-liquid extraction step A) that is fed at the top with said feedstock in a mixture with the raffinate obtained from re-extraction step B), where this mixture constitutes the feed for said step A), and at the bottom with an effluent that is rich in a specific Lewis donor solvent as described above and as obtained from regeneration step C), where it produces an extract at the top and at the bottom a purified feedstock, operating at a temperature of between 10 and 70° C. and a pressure of between 0.1 and 0.5 MPa, preferably between 0.2 and 0.4 MPa, with a continuous-phase mass flow rate/dispersed-phase mass flow rate ratio of less than 70, preferably less than 3, and preferably less than 1.5. Beyond 70, the hydrodynamic functioning of the column is compromised. Whether the Lewis donor solvent forms the continuous or the dispersed phase matters little since this criterion is a hydrodynamic criterion.

As one skilled in the art is aware, liquid-liquid extraction operates with two liquid phases, where one of the phases constitutes the continuous phase and the other constitutes the dispersed phase, which is present in the form of individual drops. Whether the nature is continuous or dispersed depends on the relative flow rate of one phase with respect to the other. Thus, as we are aware from the well-known phenomenon, if the flow rate of the continuous phase is reduced by increasing the flow rate of the dispersed phase, the dispersed phase will become continuous, and vice versa.

The Lewis donor solvent rotates through steps A), B), and C). Any losses of Lewis donor solvent are made up by means of an outside make-up of Lewis donor solvent mixed with the Lewis donor solvent-rich effluent obtained from step C). During the start-up of the method according to the invention, the Lewis donor solvent is fed at the bottom of said step A), with the flow rate of the feed being reduced as the recycling with Lewis donor solvent-rich effluent obtained from step C) takes hold, until it ultimately represents only the flow rate of any make-up.

The Lewis donor solvent-rich effluent obtained from step C) and the feedstock that feeds said step A) are each fed at temperatures that are independent of one another, between 10 and 70° C. and preferably between 40 and 55° C.

The higher the ratio of the mass flow rate of the effluent that is rich in solvent obtained from step C)/mass flow rate of the feed of said step A), the more efficient the impurity extraction step. However, a high ratio also leads to the extraction of a significant fraction of the ethanol and acetaldehyde in the extract obtained from said step A) and consequently to an increase in the flow rate of auxiliary solvent required within step B) in order to limit the losses of ethanol and acetaldehyde. The value of the ratio of mass flow rate of Lewis donor solvent-rich effluent to the mass flow rate of auxiliary solvent thus has to be adjusted in such a way as to extract the maximum amount of impurities while limiting the losses of ethanol and acetaldehyde. The higher this ratio, the more impurities will be extracted from the extract obtained from step B) and the greater will be the losses of ethanol and acetaldehyde, that is, the ethanol and acetaldehyde that are found in said extract obtained from step B).

The ratio of the mass flow rate of Lewis donor solvent-rich effluent to the mass flow rate of auxiliary solvent is adjusted in such a way that said extract obtained from step B) comprises 50% by weight, preferably 60% by weight, and in a preferred manner 70% by weight of the impurities contained in said feedstock, as well as at most 5% by weight, preferably at most 2% by weight, and in a preferred manner at most 1% by weight of the total quantities of ethanol and acetaldehyde contained in said feedstock.

Contact between the two liquid phases in said extraction section is brought about inside a liquid-liquid extractor. Different types of contact can be envisioned. In a non-limiting manner, a packed column, a pulsed column, a stirred compartmented column, or else a mixer-decanter battery can be mentioned.

Said extract from step A) feeds step B) for re-extraction of ethanol and acetaldehyde.

Surprisingly enough, the applicant has discovered that using a specific extraction solvent as described above, that is not miscible with a feedstock that contains ethanol and acetaldehyde, made it possible to keep the column from being fouled to a large extent.

Use of the extraction solvent according to the invention makes it possible to reduce operating costs by reducing the amount of solvent and by avoiding the fouling that occurs in steps A) and B)).

Step B) for Re-Extraction of Ethanol and Acetaldehyde

The purification method according to the invention comprises a counter-current liquid-liquid re-extraction step B), which is advantageously implemented inside a liquid-liquid extractor and is fed:

with an auxiliary solvent at the top,
with the extract obtained from step A) at the bottom, operating at a temperature of between 10 and 70° C. and at a pressure of between 0.1 and 0.5 MPa, preferably between 0.2 and 0.4 MPa, with a ratio of continuous-phase mass flow rate/dispersed-phase mass flow rate of less than 70, preferably less than 3, and preferably less than 1.5, since above 70, the hydrodynamic functioning of the column is compromised, and produces:

at the top, an extract that advantageously contains less than 5% of the total quantities of ethanol and acetaldehyde contained in said feedstock,
a raffinate at the bottom.

It matters little whether the auxiliary solvent forms the continuous phase or the dispersed phase since this criterion is a hydrodynamic criterion.

Said auxiliary solvent is an aqueous solution that contains at least 90% by weight water, preferably water originating from outside the process, and preferably devoid of ethanol and acetaldehyde. The use of water makes it possible to reduce the contents of ethanol and acetaldehyde in the extract of section B) and to improve the separation between the impurities and the compounds ethanol and acetaldehyde in the extraction section A) by reducing the ethanol+acetaldehyde/water ratio in said section. Said auxiliary solvent can be, for example, a stream of water obtained from a method for converting ethanol into butadiene.

Said auxiliary solvent and said extract obtained from step A) are independently fed at a temperature of between 10 and 70° C. and preferably between 40 and 55° C.

The raffinate that is produced at the bottom of said step B) is mixed with the feedstock that feeds the method according to the invention and can also feed said step A) at the top.

Contact between the two liquid phases in said re-extraction step is advantageously made inside a liquid-liquid extractor. Different modes of contact can be envisioned. In a non-limiting manner, a packed column, a pulsed column, a stirred compartmented column, or else a mixer-decanter battery can be mentioned.

Steps A) and B) are advantageously carried out in a single device.

Said extract that is obtained from re-extraction step B) feeds the regeneration section C).

Solvent Regeneration Step C)

The purification method according to the invention comprises a regeneration step C) in which the extract obtained from liquid-liquid re-extraction step B) feeds a first distillation column that produces at the top an impurity-rich distillate that is eliminated from the process and at the bottom a residue that feeds a second distillation column. Said second distillation column produces at the bottom an impurity-rich residue that is eliminated from the process and at the top an effluent that is rich in Lewis donor solvent, with said effluent then being recycled in liquid-liquid extraction step A).

The impurities can be categorized as follows:
1) "light impurities," whose boiling point is lower than the boiling point of the Lewis donor solvent and that are produced at the top of the first distillation column;
2) and "heavy impurities," whose boiling point is greater than that of the Lewis donor solvent and that are produced at the bottom of said second distillation column.

These impurities (light and heavy) correspond to a set of thousands of hydrocarbon or oxygen compounds.

Said distillate from the first distillation column is composed in the majority of "light impurities." "In the majority" is defined as more than 85% by weight and preferably more than 95% by weight. Said impurity-rich distillate can be burned to supply a portion of the heat required for the hot-oil circuit or for the steam boilers of the method for producing butadiene from ethanol and acetaldehyde.

Said effluent from the second distillation column is composed in the majority of the Lewis donor solvent. "In the majority" is defined as more than 85% by weight and advantageously more than 95% by weight. Said effluent that is rich in Lewis donor solvent is recycled to the bottom of said liquid-liquid extraction step A).

Said residue from the second distillation column is composed in the majority of "heavy impurities." "In the majority" is defined as more than 85% by weight and preferably more than 95% by weight. Said impurity-rich residue can be burned to supply a portion of the heat required for the hot-oil circuit or for the steam boilers of the method for producing butadiene from ethanol and acetaldehyde.

In another embodiment of the invention, which is adapted to the hypothetical case where the proportion of heavy impurities is small, only a fraction of the residue from said first distillation column continuously feeds said second distillation column, with the remaining fraction being recycled to said step A) since it is rich in Lewis donor solvent.

In another embodiment of the invention, which is adapted to the hypothetical case where the proportion of heavy impurities is very small, only a fraction of the residue from said first distillation column sequentially feeds said second distillation column, with the remaining fraction being recycled to said step A) since it is rich in Lewis donor solvent.

Using a solvent with a high boiling point makes it possible to reduce the operating costs of and investment costs for the solvent regeneration section C) compared to the prior art by reducing the size of said second distillation column or the frequency of its use.

Figure 1:
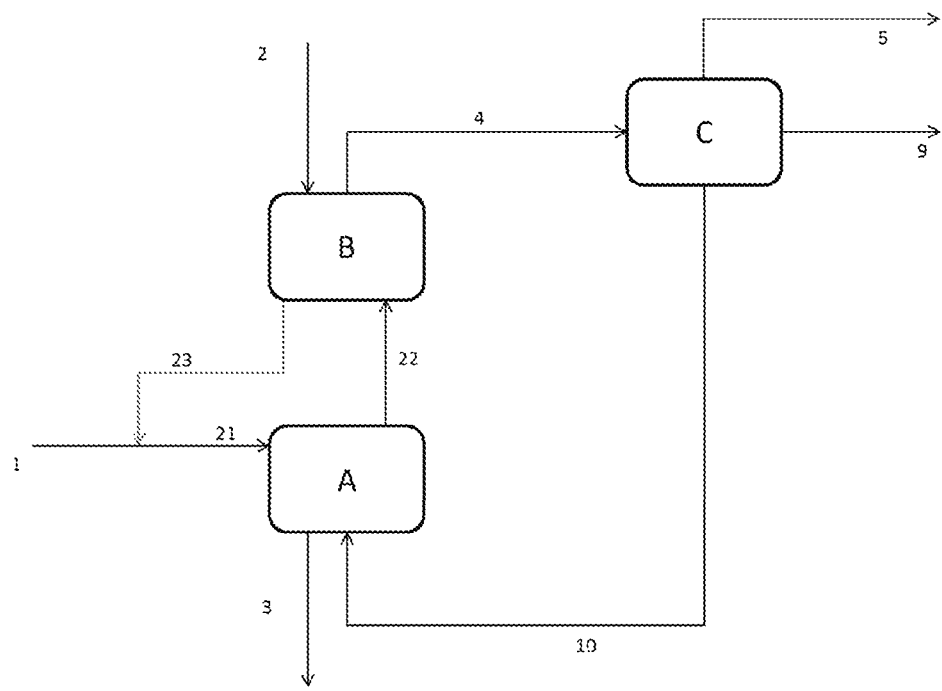
FIG. 1 depicts in schematic form a general arrangement of the method according to the invention.

A counter-current liquid-liquid extraction step A) is fed with a feedstock (1) in a mixture with the raffinate (23) obtained from re-extraction step B), where this mixture constitutes the feed (21) for said step A), and at the bottom is fed with the Lewis donor solvent-rich effluent (10) obtained from regeneration step C) and produces an extract (22) and a purified feedstock (3).

A counter-current liquid-liquid re-extraction step B) is fed with an auxiliary solvent (2) and at the bottom with the extract (22) obtained from step A) and produces at the top an extract (4) and at the bottom a raffinate (23), where said raffinate feeds said step A).

A regeneration step C) is fed with the extract (4) obtained from step B) and separates a distillate that is rich in light impurities (5), an effluent that is rich in Lewis donor solvent (10), and a residue that is rich in heavy impurities (9).

Figure 2:
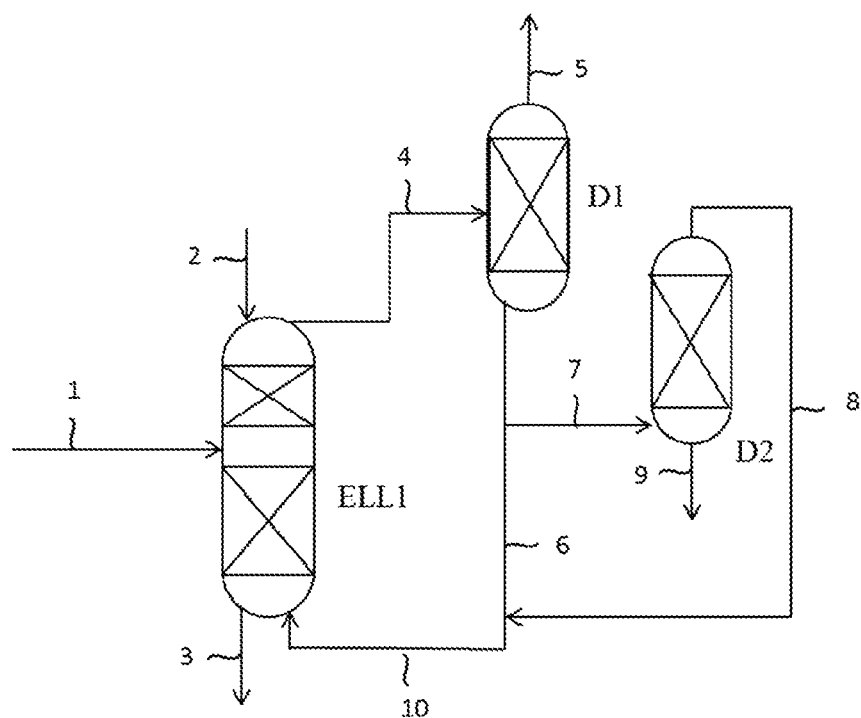

FIG. 2 depicts in schematic and non-limiting form an arrangement of the method according to the invention. The notation of the streams in FIG. 2 is identical to that in FIG. 1.

In the arrangement depicted in FIG. 2, steps A) and B) are carried out in a single device ELL 1.

The feedstock containing ethanol and acetaldehyde (1) feeds a liquid-liquid extraction column ELL1. The latter is fed at the top with an auxiliary solvent (2) and at the bottom with the Lewis donor solvent-rich effluent obtained from step C) (10). The extract (4) from step B) is drawn off at the top of the column ELL1, while the purified feedstock (3) from step A) is drawn off at the bottom of the column ELL1.

In the arrangement depicted in FIG. 2, step C) is carried out in two distillation columns D1 and D2.

The extract (4) obtained from step B) feeds a distillation column D1. A distillate rich in light impurities (5) is separated at the top, and a residue is drawn off at the bottom. When the proportion of heavy impurities in this residue is small, only a fraction (7) of said residue feeds a second distillation column D2, with the residual fraction (6) being recycled to step A) in column ELL1 in a mixture with the flow (8) as a Lewis donor solvent-rich effluent (10).

An optional Lewis donor solvent make-up (not shown) can be provided in a mixture with the Lewis donor solvent-rich effluent (10) to make up for the losses of Lewis donor or during the start-up of the process.

At the top the second distillation column D2 separates a Lewis donor solvent-rich effluent (8), which is recycled to step A) in column ELL1 in a mixture with the residual fraction (6), and at the bottom separates a residue that is rich in heavy impurities (9), which residue is eliminated from the process.

EXAMPLES

Example 1

In this example, the performance levels achieved with a solvent according to the invention are compared to the performance levels achieved with the solvents described in the prior art for a given solvent/feedstock mass ratio.

An analysis is made of the performance levels obtained for purifying the key impurities in a feedstock whose composition is similar to that of industrial effluent from a process of the Lebedev type (ethanol=50% by weight; acetaldehyde=9% by weight; water=27% by weight; impurities=14% by weight). The mass ratio of solvent to feedstock is 1.

The partition coefficient K is measured for ethyl acetate and diethyl ether between a hydroalcoholic phase and different solvents that were tested. The term "key impurities" is defined here to mean that the capacity for separating these impurities is representative of the capacity for separating the complex mixture of impurities in an actual flow.

We write $K_i=[1]_{S1}/[1]_{S2}$, where $[1]_{S1}$ is the concentration of type 1 in mol/kg in the extraction solvent, denoted S1, and $[1]_{S2}$ is a concentration of type 1 in mol/kg in the hydroalcoholic phase, denoted S2.

Selectivity for absorption of impurities i is also defined with respect to ethanol $S_{i/ethanol}=K_i/K_{ethanol}$.

Various non-compliant extraction solvents were tested:
a hydrocarbon having fewer than 12 carbon atoms: hexane a fatty acid having fewer than 12 carbon atoms: nonanoic acid
a phosphate ester having fewer than 12 carbon atoms: triethyl phosphate
a hydrocarbon having at least 12 carbon atoms: hexadecane.

These solvents are compared against the following compliant solvent:
a mixture of a hydrocarbon and a Lewis donor compound having more than 12 carbon atoms: a mixture of oleic acid and hexadecane.

The partition coefficients of the two key impurities (ethyl acetate and diethyl ether), their ethanol selectivity values, and the presence or absence of a deposit are presented in the table below and for different solvents, according to the invention and according to the prior art:

| Extraction Solvent | Hexane ($C_6$) | Nonanoic Acid ($C_9$) | Triethyl Phosphate ($C_6$) | Hexadecane ($C_{16}$) | 30% Oleic Acid ($C_{18}$) + 70% Hexadecane |
|---|---|---|---|---|---|
| Formation of a Deposit | Yes | Yes | Monophasic | Yes | No |
| $K_{ethyl\ acetate}$ | 4.7 | 4.2 | | 0.6 | 1.1 |
| $K_{diethyl\ ether}$ | 2.3 | 4.4 | | 1.4 | 2.2 |
| $S_{ethyl\ acetate}$ | 47.8 | 4.3 | | 28 | 7.6 |
| $S_{diethyl\ ether}$ | 22.8 | 4.5 | | 69 | 15.3 |

In the case of triethyl phosphate, separation is not possible because the mixture is monophasic. Hexane is an excellent extraction solvent, but the mixture with the feedstock is diphasic only under narrow conditions of concentration, making it tricky to use in liquid-liquid extraction.

It should be noted that the use in accordance with the invention of a hexadecane-oleic acid mixture leads to better extraction than with hexadecane by itself. Moreover, despite the fact that selectivity is a bit lower, the mixture does not form deposits in the equipment.

Example 2

In this example, the performance levels achieved with a solvent that is compliant with the invention are compared with solvents that have different chemical functions for a given solvent/feedstock mass ratio.

An analysis is made of the performance levels obtained in separating the impurities and brown oils of a feedstock that is close in composition to an industrial composition (ethanol=50% by weight; acetaldehyde=9% by weight; water=27% by weight; impurities=14% by weight). The solvent/feedstock mass ratio is 1.

Various non-compliant extraction solvents were tested:
a fatty-acid methyl ester composed of 18 carbon atoms: sunflower methyl ester;
an alcohol composed of 18 carbon atoms: oleic acid;
as well as the compliant solvents as follows:
a fatty acid composed of 18 carbon atoms and a double bond: oleic acid;
a fatty acid composed of 18 carbon atoms and two double bonds: linoleic acid;
an organophosphorus compound: tributyl phosphate, composed of 12 carbon atoms.

The partition coefficients of two key impurities (ethyl acetate, diethyl ether), their levels of selectivity with respect to ethanol, and the presence or absence of a deposit are given in the table below and for different solvents, according to the invention and according to the prior art:

| Extraction Solvent | Sunflower Methyl Ester | Oleic Alcohol | Oleic Acid | Linoleic Acid | Tributyl Phosphate |
|---|---|---|---|---|---|
| Formation of a Deposit | Yes | Yes | No | No | No |
| $K_{ethyl\ acetate}$ | 1.8 | 2.0 | 2.1 | 2.5 | 1.7 |
| $K_{diethyl\ ether}$ | 2.5 | 2.4 | 2.6 | 3.1 | 1.8 |
| $S_{ethyl\ acetate}$ | 4.0 | 3.6 | 2.8 | 3.6 | 1.8 |
| $S_{diethyl\ ether}$ | 17.2 | 4.4 | 3.6 | 4.6 | 2.0 |

This comparative example clearly illustrates the benefit of using a Lewis donor compound as prescribed for the purposes of the invention, where said compound makes it possible to avoid the formation of a deposit.

The invention claimed is:

1. A method for purifying a feedstock that contains ethanol, acetaldehyde, and impurities using a solvent, referred to as a Lewis donor solvent, that comprises a Lewis donor compound that is selected from the group made up of unsaturated fatty acids that have between 12 and 18 carbon atoms, phosphate esters that have between 12 and 30 carbon atoms, and mixtures thereof, where said method comprises:
a counter-current liquid-liquid extraction step A) that is fed at the top with said feedstock in a mixture with the raffinate obtained from re-extraction step B), wherein said mixture constitutes the feed for said step A), and at the bottom is fed with the Lewis donor solvent-rich effluent obtained from regeneration step C), a Lewis donor solvent make-up that may optionally be mixed with said Lewis donor solvent-rich effluent, where said step produces at the top an extract and at the bottom a purified feedstock and operates at a temperature of between 10 and 70° C. and at a pressure of between 0.1 and 0.5 MPa with a continuous-phase mass flow rate/dispersed-phase mass flow rate ratio of less than 70;
a counter-current liquid-liquid re-extraction step B) that is fed at the top with an auxiliary solvent and at the bottom with the extract obtained from step A) and that produces at the top an extract and at the bottom a raffinate, where said raffinate feeds said step A), with this step operating at a temperature of between 10 and 70° C. and at a pressure of between 0.1 and 0.5 MPa with a continuous-phase mass flow rate/dispersed-phase mass flow rate ratio of less than 70;
a regeneration step C) in which the extract obtained from step B) is separated by a first distillation into a distillate that is rich in light impurities and a residue that undergoes a second distillation, where the latter produces at the top an effluent that is rich in Lewis donor solvent and a residue that is rich in heavy impurities;
where said Lewis donor solvent comprises a Lewis donor selected from the group made up of unsaturated fatty acids that have between 12 and 18 carbon atoms, phosphate esters that have between 12 and 30 carbon atoms, and mixtures thereof.

2. The method in accordance with claim 1 in which said Lewis donor compound is selected from the group made up of oleic acid, linoleic acid, tributyl phosphate, and mixtures thereof.

3. The method in accordance with claim 1, in which said Lewis donor solvent also comprises at least one hydrocarbon that contains at least 12 carbon atoms, with the proportion (Lewis donor compound)/hydrocarbon+Lewis donor compound) falling into a range of from 1 to less than 100% by weight.

4. The method in accordance with claim 1 in which said ratio falls into a range of from 15 to less than 100% by weight.

5. The method in accordance with claim 1 in which said auxiliary solvent solution is water.

6. A process for separating impurities from a feedstock containing ethanol, acetaldehyde, and impurities, comprising subjecting the feedstock to a solvent that comprises a Lewis donor compound that is selected from the group made up of unsaturated fatty acids that have between 12 and 18 carbon atoms, phosphate esters that have between 12 and 30 carbon atoms, and mixtures thereof.

7. The process according to claim 6 in which said Lewis donor compound is selected from the group made up of oleic acid, linoleic acid, tributyl phosphate, and mixtures thereof.

8. The process according to claim 7 in which said Lewis donor compound is oleic acid.

9. The process according to claim 6 in which said solvent that comprises a Lewis donor compound also comprises at least one hydrocarbon containing at least 12 carbon atoms, with the proportion (Lewis donor compound)/hydrocarbon+Lewis donor compound) falling into a range of from 1% to less than 100% by weight.

* * * * *